United States Patent
Tichy et al.

(10) Patent No.: US 7,473,675 B2
(45) Date of Patent: Jan. 6, 2009

(54) DISINFECTANT SYSTEMS AND METHODS COMPRISING A PERACID, ALCOHOL, AND TRANSITION METAL

(75) Inventors: Daryl J. Tichy, Orem, UT (US); Brian G. Larson, Alpine, UT (US)

(73) Assignee: Solutions BioMed, LLC, Orem, UT (US)

( * ) Notice: Subject to any disclaimer, the term of this patent is extended or adjusted under 35 U.S.C. 154(b) by 110 days.

(21) Appl. No.: 11/514,721

(22) Filed: Aug. 31, 2006

(65) Prior Publication Data

US 2007/0059202 A1 Mar. 15, 2007

Related U.S. Application Data

(63) Continuation-in-part of application No. 11/361,836, filed on Feb. 24, 2006, and a continuation-in-part of application No. 11/361,841, filed on Feb. 24, 2006, and a continuation-in-part of application No. 11/361,837, filed on Feb. 24, 2006, and a continuation-in-part of application No. 11/361,665, filed on Feb. 24, 2006.

(60) Provisional application No. 60/656,723, filed on Feb. 25, 2005.

(51) Int. Cl.
C11D 7/18 (2006.01)
C11D 3/48 (2006.01)

(52) U.S. Cl. .............. 510/372; 510/161; 510/199; 510/235; 510/238; 510/302; 510/309; 510/319; 510/362; 510/370; 510/367; 510/375; 510/382; 510/432

(58) Field of Classification Search ............... 510/372, 510/161, 199, 235, 238, 302, 309, 319, 362, 510/370, 367, 375, 382, 432
See application file for complete search history.

(56) References Cited

U.S. PATENT DOCUMENTS

| | | |
|---|---|---|
| 716,077 A | 12/1902 | Morrin |
| 734,467 A | 7/1903 | Martien |
| 2,103,999 A | 12/1937 | Muller et al. |
| 2,304,104 A | 12/1942 | Klabunde et al. |
| 4,021,338 A | 5/1977 | Harkin |
| 4,297,298 A | 10/1981 | Crommelynch et al. |
| 4,311,598 A | 1/1982 | Verachtert |
| 4,321,255 A | 3/1982 | Boden |
| 4,414,127 A | 11/1983 | Fu |
| 4,655,975 A | 4/1987 | Snoble |
| 4,826,658 A | 5/1989 | Kay |
| 4,915,955 A | 4/1990 | Gomori |
| 5,349,083 A | 9/1994 | Brougham et al. |
| 5,357,636 A * | 10/1994 | Dresdner et al. ............ 2/161.7 |
| 5,368,867 A | 11/1994 | Da Silva et al. |
| 5,419,908 A | 5/1995 | Richter et al. |
| 5,437,858 A | 8/1995 | Hungerbach et al. |
| 5,508,046 A | 4/1996 | Cosentino et al. |
| 5,563,132 A | 10/1996 | Bodaness |
| 5,709,870 A | 1/1998 | Yoshimura et al. |
| 5,824,267 A | 10/1998 | Kawasumi et al. |
| 5,945,032 A | 8/1999 | Breitenbach et al. |
| 5,951,993 A | 9/1999 | Scholz et al. |
| 5,977,403 A | 11/1999 | Byers |
| 5,997,585 A | 12/1999 | Scialla et al. |
| 6,027,469 A | 2/2000 | Johnson |
| 6,114,298 A | 9/2000 | Petri et al. |
| 6,197,814 B1 | 3/2001 | Arata |
| 6,200,946 B1 | 3/2001 | Blum et al. |
| 6,231,848 B1 | 5/2001 | Breitenbach et al. |
| 6,242,009 B1 | 6/2001 | Batarseh et al. |
| 6,257,253 B1 | 7/2001 | Lentsch et al. |
| 6,277,414 B1 | 8/2001 | Elhaik et al. |
| 6,302,968 B1 | 10/2001 | Baum et al. |
| 6,368,611 B1 | 4/2002 | Whitbourne et al. |
| 6,379,712 B1 | 4/2002 | Yan et al. |
| 6,436,342 B1 | 8/2002 | Petri et al. |

(Continued)

FOREIGN PATENT DOCUMENTS

GB 2189394 10/1987

(Continued)

OTHER PUBLICATIONS

The interaction of silver ions and hydrogen peroxide in the inactivation of *E coli*; a preliminary evaluation of a new long lasting residual drinking water disinfectant; Water Science and Technology vol. 31 No. 5-6 pp. 123-129 (1995).

(Continued)

*Primary Examiner*—Charles I Boyer
(74) *Attorney, Agent, or Firm*—Thorpe North & Western LLP

(57) ABSTRACT

The present invention is drawn to disinfectant systems and methods which can be used to produce a disinfectant solution. The system can include a first liquid composition and a second liquid composition. The first liquid composition comprises from 0.0005 ppm to 100,000 ppm by weight of a transition metal or alloy and an alcohol, and the second liquid composition comprises water and a peroxygen compound. The first and second liquid compositions are formulated to be combined so as to yield a resultant disinfectant solution. The disinfectant solution can be used to disinfect a variety of surfaces and even liquid compositions.

85 Claims, No Drawings

U.S. PATENT DOCUMENTS

| | | | |
|---|---|---|---|
| 6,540,791 | B1 | 4/2003 | Dias |
| 6,569,353 | B1 | 5/2003 | Giletto et al. |
| 6,583,176 | B2 | 6/2003 | Arata |
| 6,630,172 | B2 | 10/2003 | Batarseh |
| 6,660,289 | B1 | 12/2003 | Wilmotte et al. |
| 6,743,348 | B2 | 6/2004 | Holladay et al. |
| 6,797,302 | B1 | 9/2004 | Ben Yehuda et al. |
| 6,827,766 | B2 | 12/2004 | Carnes et al. |
| 6,939,564 | B2 | 9/2005 | Ranger et al. |
| 6,939,566 | B2 | 9/2005 | Batarseh et al. |
| 7,033,511 | B2 | 4/2006 | Zawada et al. |
| 2003/0008797 | A1 | 1/2003 | Hage et al. |
| 2003/0099717 | A1 | 5/2003 | Cabrera |
| 2003/0235623 | A1 | 12/2003 | Van Oosterom |
| 2004/0067159 | A1 | 4/2004 | Carnes et al. |
| 2004/0170742 | A1 | 9/2004 | Ben Yehuda et al. |
| 2004/0234569 | A1 | 11/2004 | Nakada et al. |
| 2005/0013836 | A1 | 1/2005 | Raad |
| 2005/0194357 | A1 | 9/2005 | Liu et al. |
| 2005/0256017 | A1 | 11/2005 | Dykstra |
| 2005/0256200 | A1 | 11/2005 | Burkhart et al. |
| 2006/0035808 | A1 | 2/2006 | Ahmed et al. |
| 2006/0182813 | A1 | 8/2006 | Holladay |
| 2006/0198798 | A1 | 9/2006 | Tichy et al. |
| 2006/0198876 | A1 | 9/2006 | Tichy et al. |
| 2006/0199752 | A1 | 9/2006 | Tichy et al. |
| 2006/0240381 | A1 | 10/2006 | Rizoiu et al. |
| 2006/0263239 | A1 | 11/2006 | Tichy et al. |
| 2007/0048175 | A1 | 3/2007 | Tichy et al. |
| 2007/0053850 | A1 | 3/2007 | Tichy et al. |
| 2007/0059255 | A1 | 3/2007 | Tichy et al. |
| 2007/0254044 | A1 | 11/2007 | Karandikar et al. |
| 2008/0000931 | A1 | 1/2008 | Tichy et al. |

FOREIGN PATENT DOCUMENTS

| | | |
|---|---|---|
| WO | WO 03/080231 | 10/2003 |
| WO | WO 2005/000324 | 1/2005 |
| WO | WO2006/076109 | 7/2006 |

OTHER PUBLICATIONS

U.S. Appl. No. 11/891,316; Tichy et al., filed Aug. 8, 2007.

Schuster, A. et al., "Persistent silver disinfectant for the environment: Myth and reality," Am. J. Infect. Control, Jun. 2003, pp. 309-311, vol. 32.

Brady, Michael J. et al., "Persistent silver disinfectant for the environmental control of pathogenic bacteria," Am. J. Infect. Control, Aug. 2004, pp. 208-214, vol. 31 (4).

Brentano, Loreno et al., "Antibacterial efficacy of a colloidal silver complex," Surg. Forum, 1966, pp. 76-78, vol. 17.

Phillips, Charles R., et al., "Chemical Disinfectant," Annual Review of Microbiology, Oct. 1958, pp. 525-550, vol. 12.

Monarca, S. et al, "Decontamination of dental unit waterlines using disinfectants and filters," Abstract Only, Minerva Stomatol., Oct. 2002, vol. 10.

Yin, Huiyong, "Analysis of Diacyl Peroxides by Ag+ Coordination Ionspray Tandem Mass Spectrometry: Free Radical Pathways of Complex Decomposition," J. Am. Soc. Mass Spectrum, Apr. 2001, pp. 449-455, vol. 12 (4).

Surdeau, N. et al, Sensitivity of bacterial viofilms and planktonic cells to a new antimicrobial agent, Oxsil 320N, Journal of Hospital Infection 2006, 62, 487-493, www.elsevierhealth.com/journals/jhin.

http://web.archive.org/web/20060217191603/http://sanosilbiotech.com/start_food.html, Virosol F&B, "Swift Virucidal with Swiss Precision," Feb. 17, 2006, 5 pages.

* cited by examiner

DISINFECTANT SYSTEMS AND METHODS COMPRISING A PERACID, ALCOHOL, AND TRANSITION METAL

The present application is a continuation-in-part of U.S. patent application Ser. Nos. 11/361,836; 11/361,841; 11/361,837; and 11/361,665, each of which was filed on Feb. 24, 2006, each of which claims the benefit of U.S. Provisional Patent Application No. 60/656,723, filed on Feb. 25, 2005.

FIELD OF THE INVENTION

The present invention is drawn to disinfectant systems and methods which are suitable for consumer use in disinfecting a variety of surfaces and solutions. The system is convenient, easy and safe to use.

BACKGROUND OF THE INVENTION

Disinfectants, such as hard surface disinfectants, are widely used in both domestic and professional settings. Exemplary of a commonly used hard surface cleaner is Lysol® disinfectant. Though Lysol® is effective for many applications; Lysol® is not as effective at reducing levels of bacterial endospores as commercially available glutaraldehyde aqueous solutions. Glutaraldehyde aqueous solutions are widely used as disinfectants, and are commonly available in 1 wt % and 2 wt % solutions, particularly in medical and dental settings. Glutaraldehyde solutions are typically used for more delicate medical/dental instruments that would otherwise be susceptible to damage by other sterilization methods, e.g., autoclaving. However, glutaraldehyde is also a powerful irritant and respiratory sensitizer. In fact, there have been reports of sensitization of individuals due to the fumes, which have lead to respiratory problems, headaches, lethargy, discoloring of the skin, etc. Because of these issues related to glutaraldehyde fumes, air quality must often be monitored, or appropriate air ventilation must be present. As a result, though glutaraldehyde solutions are relatively effective disinfectants, it would be desirable to provide compositions that can exhibit even more effective bacteria kill levels, and at the same time be safer for the individuals using the disinfectant.

SUMMARY OF THE INVENTION

It has been recognized that it would be desirable to provide a system for convenient and easy preparation of a disinfectant solution. In accordance with this, a two-part disinfectant system and method is provided. The two-part disinfectant system includes a first liquid composition and a second liquid composition. The first liquid composition can comprise from 0.0005 ppm to 100,000 ppm by weight of a transition metal or alloy and an alcohol, and the second liquid composition can comprise water and a peroxygen compound. The first and second liquid compositions can be formulated to be combined so as to yield a resultant disinfectant solution.

In another embodiment, a method of disinfecting a surface can comprise admixing a first liquid composition and a second liquid composition to form a resultant disinfectant composition. The first liquid composition can comprise from 0.0005 ppm to 100,000 ppm by weight of a transition metal or alloy and an alcohol, the second liquid composition can comprise water and a peroxygen compound. The method further comprises contacting the resultant disinfectant with a surface, thereby disinfecting the surface. The contacting can occur after the resultant disinfectant is formed, or can form after both parts are contacted with the surface.

In another embodiment, a method of disinfecting and providing residual kill at a surface can comprise contacting the surface with a disinfectant solution which includes from 0.0005 ppm to 50,000 ppm by weight of a transition metal or alloy, an alcohol, a peroxygen compound, and water. Then, after drying, residual components of the disinfectant solution are allowed to remain on the surface causing residual kill to bacterial, viral, or fungal organisms that subsequently contact the surface.

Additional features and advantages of the invention will be apparent from the detailed description that follows, which illustrates, by way of example, features of the invention.

DETAILED DESCRIPTION OF THE PREFERRED EMBODIMENT(S)

Reference will now be made to the exemplary embodiments, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention. It is also to be understood that the terminology used herein is used for the purpose of describing particular embodiments only. The terms are not intended to be limiting unless specified as such.

It must be noted that, as used in this specification and the appended claims, the singular forms "a," "an," and "the" include plural referents unless the content clearly dictates otherwise.

The term "food grade" when used with respect to a composition of the present invention refers to a composition that is substantially free from ingredients which would be considered harmful or toxic to a mammal upon consumption above levels that are generally recognized as safe.

Generally, though sanitizers, sterilants, and disinfectants are used for the same purpose, i.e. to kill bacteria and/or viruses, etc., a sterilant composition exhibits a greater kill level compared to a disinfectant, which in turn has a better kill level than a sanitizer. This being stated, most applications require only sanitizer or disinfectant levels bacteria/virus reduction, though other applications benefit considerably from the use of sterilants. For convenience, in the present disclosure, the term "disinfectant" is used generally and includes sanitizers, disinfectants, and sterilants unless the context dictates otherwise.

The term "solution" is also used throughout the specification to describe the disinfectant compositions of the present invention. However, as these "solutions" can include colloidal transition metals, these compositions can also be described as dispersions or suspensions. As the continuous phase is typically a solution, and the transition metal can be present in ionic and/or colloidal form, for convenience, these compositions will typically be referred to as "solutions" herein. Further, sometimes a disinfectant solution is referred to as a "resultant" disinfectant solution. This is to provide clarity that the disinfectant solution is a product of the mixing of the two-part systems described herein. This being stated, the terms "disinfectant solution" and "resultant disinfectant solution" can be used interchangeably herein.

The term "substantially free" when used with regard to the disinfectant compositions of the present invention refers to the total absence of or near total absence of a specific compound or composition. For example, when a composition is said to be substantially free of aldehydes, there are either no aldehydes in the composition or only trace amounts of aldehydes in the composition.

The term "peroxygen" refers to any compound containing a dioxygen (O—O) bond. Dioxygen bonds, particularly bivalent O—O bonds, are readily cleavable, thereby allowing compounds containing them to act as powerful oxidizers. Non-limiting examples of classes of peroxygen compounds include peracids, peracid salts, and peroxides such as hydrogen peroxide.

When referring to the term "alloy," it is understood that individual colloidal or metallic particles can be in the form of composites of multiple metals, or alloys can also include co-dispersions of multiple metals as separate particles.

The term "alcosol" is a term of art which refers to a solution of an alcohol and a colloidal metal (e.g. colloidal silver). Some alcosols may include some amount of water in addition to the alcohol and colloidal metal. Similarly, the term "hydrosol" is a term of art which refers to a solution of water and colloidal metal (e.g. colloidal silver).

The term "two-part" when referring to the systems of the present invention is not limited to systems having only two parts. For example, the system can be a concentrate, and thus, is actually a three part system, e.g., a first part including transition metal and alcohol, a second part including a peroxygen and water, and a third part of a diluting solvent for diluting the first part, the second part, and/or the resultant disinfectant solution). Non-limiting examples of diluting solvents include water, alcohols, or combinations thereof. When the diluting solvent is an alcohol, it can, but need not be the same alcohol or mixture of alcohols which are present in the first "part" of the system. Thus, "two-part" is specifically defined herein to mean, at least two parts, unless the context dictates otherwise.

Concentrations, dimensions, amounts, and other numerical data may be presented herein in a range format. It is to be understood that such range format is used merely for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a weight ratio range of about 1 wt % to about 20 wt % should be interpreted to include not only the explicitly recited limits of 1 wt % and about 20 wt %, but also to include individual weights such as 2 wt %, 11 wt %, 14 wt %, and sub-ranges such as 10 wt % to 20 wt %, 5 wt % to 15 wt %, etc. In accordance with this, two-part disinfectant system can comprise a first liquid composition and a second liquid composition. The first liquid composition can comprise from 0.0005 ppm to 100,000 ppm by weight of a transition metal or alloy and an alcohol, and the second liquid composition can comprise water and a peroxygen compound. The first and second liquid compositions can be formulated to be combined so as to yield a resultant disinfectant solution.

In another embodiment, a method of disinfecting a surface can comprise admixing a first liquid composition and a second liquid composition to form a resultant disinfectant composition. The first liquid composition can comprise from 0.0005 ppm to 100,000 ppm by weight of a transition metal or alloy and an alcohol, the second liquid composition can comprise water and a peroxygen compound. The method further comprises contacting the resultant disinfectant with a surface, thereby disinfecting the surface. The contacting can occur after the resultant disinfectant is formed, or can form after both parts are contacted with the surface.

In these embodiments, it is notable that the concentrations of each ingredient can be described in the context of concentration in the first or second liquid composition, or the resultant disinfectant solution. The concentration of a compound in the first or second liquid composition will usually be lower in the resultant disinfectant solution than in the first or second liquid composition, as the amount typically gets diluted by the other part of the system. This being stated, this is not always the case, depending on the ingredients in the other portion of the two-part system.

In embodiments of the present invention, the alcohol can be present in the first liquid composition at from about 0.005 wt % to 99.99 wt %, with the upper end of the range being modifiable to 80 wt % or 50 wt %, and the lower end of the range being modifiable to 0.05 wt % or 0.1 wt %. This being stated, it is also noted that in certain embodiments, the alcohol can be present in the resultant disinfectant solution at from 0.001 wt % to 95 wt %, with the lower end of the range being modifiable to 0.05 wt % or 0.1 wt %, and the upper end of the range being modifiable to 40 wt %, 30 wt %, 20 wt % or 10 wt % in accordance with embodiments of the present invention. Any combination of these upper and lower limits is included herein.

Regarding the transition metal or alloy present in the first liquid composition, the range of 0.0005 ppm to 100,000 ppm by weight can be modified at the upper end of the range to 20,000 ppm or 5,000 ppm, and/or can be modified at the lower end of the range to 0.001 ppm, 0.01 ppm, or 1 ppm. The resultant disinfectant solution, on the other hand, can include from 0.001 ppm to 50,000 ppm by weight of the transition metal or alloy thereof. This range can be modified at the upper end of the range to 10,000 ppm, 5,000 ppm, or 1,500 ppm, and at the lower end of the range from 0.1, 1, or 15, for example. Any combination of these upper and lower limits is included herein.

Regarding the second liquid composition, water and the peroxygen compound can be present at various ratios. For example, the peroxygen can be present in the second liquid composition at from 0.001 wt % to 80 wt %, with the upper end of the range being modifiable to 30 wt % or 15 wt %, and the lower end of the range being modifiable to 0.01 wt % or 0.05 wt %. Regarding the resultant disinfectant solution, the peroxygen content can be, for example, from 0.01 wt % to 20 wt %, with the upper end of the range being modifiable to 10 wt %, 5 wt %, or 2 wt %, and the lower end of the range being modifiable to 0.01 wt %, 0.2 wt %, or 0.3 wt %. Again, any combination of these upper and lower limits is included herein.

As these ranges are merely exemplary, one skilled in the art could modify these ranges for a particular application, considering such things as the type of alcohol (polyhydric, food grade, mixtures, etc.); the type of peroxygen (peroxide, peracid, combination of peroxide/peracid, etc.); and the type of metal (ionic, colloidal, alloy, etc.).

The systems and methods can be formulated and packaged in any manner known to those skilled in the art so long as it allows the two liquid compositions of the system to remain separate until shortly before the desired use of the disinfectant solution. In one embodiment, the two liquid compositions of the system can be contained in separate containers such as bottles, jars, bags, dispensers, etc. In one aspect of the invention, the system can be configured and the liquid compositions formulated so that the disinfectant solution can be made from the two liquid compositions alone. In another aspect of the invention, the two liquid compositions of the system can be formulated to provide a concentrate of the disinfectant solution which can be diluted to a desired disinfectant potency level with water or other diluting solvent(s).

In another embodiment of the present invention, the two liquid compositions of the system can be placed in separate compartments of a single container. For example, the system can comprise a two compartment container, each compartment having a separate extraction tube for extracting the liquid compositions in the compartments. In one aspect, the container can include a spray nozzle connected to the two extraction tubes. The two liquid compositions can be drawn up the extraction tubes to a mixing chamber within the spray nozzle and then discharged from the nozzle and onto the surface being disinfected. In this embodiment, the disinfectant solution is effectively made in small batches within the mixing chamber and discharged for use shortly after combination of the two liquid compositions.

The system is convenient, easy to use and package, and has a prolonged shelf life. Typically, disinfectant compositions containing peroxygen compounds degrade fairly quickly when combined with other agents, therefore rendering their shelf life undesirably short. The present invention provides a system which maintains the peroxygen compound separate from the rest of the disinfectant solution until shortly before its use. Such a configuration of the system allows for the disinfectant solution to effectively have a prolonged shelf life. This is particularly helpful where the liquids of the system are intended to be sold in retail and wholesale businesses, as storage, transportation, and end point shelf times can be substantial.

In one embodiment, the disinfectant solution, and hence the two liquid compositions of the two-part system, can include only ingredients that are food-grade or food safe. For example, though not required, the composition can be substantially free of disinfectant ingredients commonly present in many commercially available surface cleaners. Examples of non-food-grade ingredients which can be omitted from the disinfectant solution include, but are not limited to, aldehydes such as glutaraldehyde; chlorine-based disinfectants; chlorine and bromine-based disinfectants; iodophore-based disinfectants; phenolic-based disinfectants, quaternary ammonium-based disinfectants; and the like.

The liquid compositions of the present invention can also include other ingredients, such as organic co-solvents, surfactants, excipients, fillers, colorant, other active ingredients, ingredients that may be present in the other part, etc. In one embodiment, the first liquid composition can include water in addition to the alcohol.

Examples of alcohols which can be used in the first liquid composition include but are limited to aliphatic alcohols and other carbon-containing alcohols, having from 1 to 24 carbons ($C_1$-$C_{24}$ alcohol). It is to be noted that "$C_1$-$C_{24}$ alcohol" does not necessarily imply only straight chain saturated aliphatic alcohols, as other carbon-containing alcohols can also be used within this definition, including branched aliphatic alcohols, alicyclic alcohols, aromatic alcohols, unsaturated alcohols, as well as substituted aliphatic, alicyclic, aromatic, and unsaturated alcohols, etc. In one embodiment, the aliphatic alcohols can be $C_1$, to $C_5$ alcohols including methanol, ethanol, propanol and isopropanol, butanols, and pentanols, due to their availability and lower boiling points. This being stated, polyhydric alcohols can also be used effectively in enhancing the disinfectant and sterilant potency of the disinfectant solution of the present invention, as well as provide some degree of added stabilization. Examples of polyhydric alcohols which can be used in the present invention include but are not limited to ethylene glycol (ethane-1,2-diol) glycerin (or glycerol, propane-1,2,3-triol), and propane-1,2-diol.

Other non-aliphatic alcohols may also be used including but not limited to phenols and substituted phenols, erucyl alcohol, ricinolyl alcohol, arachidyl alcohol, capryl alcohol, capric alcohol, behenyl alcohol, lauryl alcohol (1-dodecanol), myristyl alcohol (1-tetradecanol), cetyl (or palmityl) alcohol (1-hexadecanol), stearyl alcohol (1-octadecanol), isostearyl alcohol, oleyl alcohol (cis-9-octadecen-1-ol), palmitoleyl alcohol, linoleyl alcohol (9Z,12Z-octadecadien-1-ol), elaidyl alcohol (9E-octadecen-1-ol), elaidolinoleyl alcohol (9E,12E-octadecadien-1-ol), linolenyl alcohol (9Z,12Z,15Z-octadecatrien-1-ol), elaidolinolenyl alcohol (9E,12E,15-E-octadecatrien-1-ol), combinations thereof, and the like.

In some embodiments, for practical considerations, methanol, ethanol, and denatured alcohols (mixtures of ethanol and smaller amounts of methanol, and optionally, minute amounts of benzene, ketones, acetates, etc.) can often be preferred for use because of their availability and cost. Glycerol can also be preferred in some embodiments. If the desire is to provide a food grade composition, then alcohols can be selected that satisfy this requirement. When considering the amount of alcohol to use, one skilled in the art can stay within the above-described ranges, or modify these ranges for a particular application, considering such things as whether alcohol selected for use is polyhydric, whether the alcohol is food grade, mixtures of alcohols, etc.

Regarding the transition metal present in the first liquid composition, and ultimately in the disinfectant solution, the metal can be in ionic form (e.g. disassociate metal salt, metal ions from elemental metal, etc.) and/or in colloidal form. In one specific embodiment, the transition metal can be in a sub-micron form (i.e. dispersion of less than 1 μm metal colloidal particles). However, larger colloidal transition metal particles can also be used in certain applications. Typical transition metals that are desirable for use include Group VI to Group XI transition metals, and more preferably, can include Group X to Group XI transition metals. Alloys including at least one metal from the Group VI to Group Xl metals can also be used. As shown below in the examples, some alloys can enhance or increase the disinfectant potency of the present invention. It is recognized that any of these metals will typically be oxidized to the corresponding cation in the presence of a peroxygen. However, with colloidal metals, typically, the surface is usually more susceptible to such oxidation. Further, when colloidal metals are dispersed in a colloidal solution, there is often an amount of the metal in ionic or salt form that is also present in the suspension solution. For example, colloidal silver may include a certain percentage of silver salt or ionic silver in solution, e.g., 10% to 90% by weight of metal content can be ionic based on the total metal content. This being stated, certain preferred metals for use in accordance with embodiments of the present invention are ruthenium, rhodium, osmium, iridium, palladium, platinum, copper, gold, silver, manganese, zinc, alloys thereof, and mixtures thereof. Silver is often the most preferred, but metal choice can be dependent to some degree on the application, the levels of kill desired or required, the type of pathogen being targeted, the substrate that is being cleaned, etc.

It is also noted that any of these embodiments can often also benefit from the use of alloys. For Example, certain combinations of metals in an alloy may provide an acceptable kill level for a specific pathogen, and also provide benefits that are related more to secondary consideration, such as solution stability, substrate to be cleaned, etc. Preferred examples of transition metal alloys for use in the present invention include but are not limited to copper-silver alloys, silver-manganese alloys, iron-copper alloys, chromium-silver alloys, gold-silver alloys, magnesium-silver alloys, and the like.

Exemplary colloidal silvers that can be used in the first liquid composition include those sold by Solutions IE, Inc. under the trade names CS Plus and CS Ultra. Other colloidal silver products that can be used as the silver source include ASAP, Sovereign Silver, Silver Max, and the like. In one embodiment, the colloidal particles used in the present invention can have a particle size range of from 0.001 µm to 1.0 µm. In another embodiment the colloidal transition metal particles can have a size range of from 0.030 µm to 0.5 µm. In still another embodiment the average particle size is 0.35 µm to 0.45 µm. If used in ionic form, preferred silver salts include but are not limited to silver nitrate, silver acetate, silver citrate, silver oxide, and/or silver carbonate. Though many colloidal silver solutions or ionic silver solutions that are functional for use in the formulations of the present invention can be used, in one embodiment, it can be desirable to use RO water as the suspension medium for the colloidal and/or ionic silver that is mixed with the other ingredients. In a more detailed aspect, the RO water can also be distilled, resulting in 18-20 MΩ water, though this is not required.

The peroxygen component of the second liquid composition, and ultimately the disinfectant solution, can be a single compound or a combination of multiple peroxygen compounds or peroxygen forming compounds. In one embodiment, the peroxygen can be any aliphatic or aromatic peracid (or peroxyacid) that is functional for disinfectant purposes in accordance with embodiments of the present invention. While any functional peroxyacid can be used, peroxyacids containing from 1 to 7 carbons are the most practical for use. These peroxyacids can include, but not be limited to, peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, and/or peroxybenzoic acid. The peroxyacid used in the present invention can be prepared using any method known in the art. When the peroxyacid is prepared from an acid and hydrogen peroxide, the resultant mixture contains both the peroxyacid and the corresponding acid that it is prepared from. For example, in embodiments that utilize peroxyacetic acid, the presence of the related acid (acetic acid) provides stability to the mixture, as the reaction is an equilibrium between the acid, hydrogen peroxide, and the peroxyacid and water, as follows:

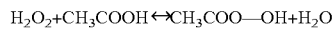

$$H_2O_2 + CH_3COOH \leftrightarrow CH_3COO\text{—}OH + H_2O$$

Peracid salts, such as salts of the above listed peracids, can also be included as the peroxygen component of the disinfectant solutions. Non-limiting examples of such salts include permanganates, perborates, perchlorates, peracetates, percarbonates, persulphates, and the like. The salts can be used alone or in combination with each other or other peroxygen compounds to form the peroxygen component of the invention.

In another embodiment, the peroxygen component of the invention can include a peroxide compound. While hydrogen peroxide is considered to be a desirable peroxide for use in accordance with embodiments of the present invention, other peroxides can also be used, such as metal peroxides and peroxyhydrates. The metal peroxides that can be used include, but are not limited to, sodium peroxide, magnesium peroxide, calcium peroxide, barium peroxide, and/or strontium peroxide. Other salts (for example sodium percarbonate) have hydrogen peroxide associated therewith much like waters of hydration, and these could also be considered to be a source of hydrogen peroxide, thereby producing hydrogen peroxide in situ. As mentioned above, the peroxides can be used alone or in combination with other peroxygen compounds to form the peroxygen component of the present invention. In one embodiment the peroxygen is a peracid and a peroxide.

Once the disinfectant solution of the present invention is formed using the system, it can be used to disinfect any number of objects using any number of contacting methods. For example, the disinfectant solution can be used as a liquid dispersion bath for objects such as instruments or as a spray for applying to less mobile objects. The disinfectant solution can also be used as a topical dressing or a mouthwash. In other words, any application method known by those skilled in the art can be utilized in accordance with embodiments of the present invention. Other possible applications or methods of use for the disinfectant solution include without limitation use as a wipe where the liquid dispersion is applied to a fabric or fabric-like material for easy application without the need for spray or other application methods, use as a topical dressing, use as a mouthwash, etc. In other words, any application method known by those skilled in the art can be utilized in accordance with embodiments of the present invention.

Additionally, though the disinfectant solution of the present invention is described generally as a disinfectant, it is recognized that there are many possible applications including its use as a sterilant or sanitizer. For example, without limitation, the disinfectant solution of the present invention can be used to kill bacteria, spores, viruses, parasites, funguses, and molds. As described, this composition can be used against all of these types of organisms with relative to complete safety to humans and other mammals.

Another feature of the disinfectant solutions of the present invention is that they have residual kill properties. Residual kill properties refer to the ability of the disinfectant solution to prevent the growth of or kill newly introduced organisms. For example, when a disinfectant solution made by the system of the present invention is applied to a surface, they act to kill existing bacteria, viruses, and/or funguses. The residual kill characteristic of the disinfectant solutions allow the solutions to continue to kill any newly introduced pathogens which may contact the surface, even after the evaporation of the solvents in the disinfectant solutions. The disinfectant solutions of the present invention are capable of providing residual kill characteristics to a contacted surface for long periods of time so long as the disinfectant solutions are not mechanically removed (e.g. washing, scraping, etc). In some embodiments, the residual kill can last for 15 days or more. In some instances when colloidal metal is present, the colloidal metal can remain on the surface indefinitely, providing antibacterial and/or anti-viral benefits for long periods of time. Alternatively, if it is desired to maintain residual kill characteristics on a surface for a period of time longer than 15 days, additional applications of the disinfectant solution can be made. In this way the disinfectant solution can also be used a prophylactic against pathogens. It is noteworthy that the residual kill property of the disinfectant solution is present regardless of the mode of preparation of the solution. In other words, a disinfectant solution prepared using the two-part disinfectant system of the present invention and one prepared using direct admixing of each of the same individual ingredients both have the residual kill property. Without being bound by any particular theory, it is believed that the metal content contributes to this residual kill, as the metal content can remain on the surface in elemental form, without degrading or evaporating.

Because the disinfectant solution can be formulated to be very safe, e.g., often including only food grade components, these compositions can be used in areas which extend well beyond their use as surface disinfectants. Such product categories include both topically and internally applied products for both humans and animals. For example, the disinfectant solution can be used for antiseptics, burn treatments, diaper rash products, and various skin care products. Alternatively, the disinfectant solutions can be used inside the mouth, such as for mouthwashes, toothpastes, and various other disinfecting solutions that are be employed in dental mold materials. As dental molds are known to spread significant disease in the dental industry, such use with dental molds can prevent or reduce the spread of pathogens from a patient's mouth to lab employees working with the finished molds. Still a further category of use includes application for antibiotic and antiviral purposes. The disinfectant solution can be formulated into lozenges or gums for application to the mouth and throat, and can even be administered orally, intramuscularly, intravenously, etc. Because of the kill levels that can be achieved, even when formulated with only food grade components, a wide range of pathogens, as well as some viruses, can be killed internally. Without being bound by any particular possibility, these compositions can be useful in killing various viruses such as HIV, SARS, West Nile, Bird Flu, and others.

EXAMPLES

The following examples illustrate the embodiments of the invention that are presently best known. However, it is to be understood that the following are only exemplary or illustrative of the application of the principles of the present invention. Numerous modifications and alternative compositions, methods, and systems may be devised by those skilled in the art without departing from the spirit and scope of the present invention. The appended claims are intended to cover such modifications and arrangements. Thus, while the present invention has been described above with particularity, the following examples provide further detail in connection with what are presently deemed to be the most practical and preferred embodiments of the invention.

Example 1

Preparation of a Disinfectant Solution Using a Two-part System

A two-part disinfectant system is provided. The first liquid composition of the system includes a solution of 20 parts by weight glycerol, 29.97 parts water and 0.03 parts colloidal silver (600 ppm). The second liquid composition includes, by weight, 1.3 parts peracetic acid and 48.7 parts water. The two components are kept separate until immediately before the disinfectant is desired for use. The disinfectant solution is made by mixing the two components at about a 1:1 (first:second) weight ratio to yield a composition having about 1.3 wt % peracetic acid and about 300 ppm silver. In this embodiment, less than 3 wt % of hydrogen peroxide can be added to further stabilize the system. This disinfectant solution can be used effectively to disinfect and sterilize a variety of surfaces.

Example 2

Preparation of a Disinfectant Solution Using a Two-part System

A two-part disinfectant system is provided. The first liquid composition of the system includes a solution of about 10 parts by weight glycerol and about 81 parts by weight of a silver hydrosol (300 ppm colloidal silver). The second liquid composition of the system is includes an aqueous solution of 15 wt % peracetic acid in water. The two components are kept separate until immediately before the disinfectant is desired for use. The two components are combined at a weight ratio of 91:9 (first:second), yielding a solution having about 1.3 wt % peracetic acid. This disinfectant solution can be used effectively to disinfect and sterilize a variety of surfaces. It is noted that there will be less than 300 ppm by weight of the colloidal silver when based on the resultant disinfectant composition as a whole. This disinfectant solution can be used effectively to disinfect and sterilize a variety of surfaces.

Example 3

Preparation of a Disinfectant Solution Using a Two-part System

A two-part disinfectant system is provided. The liquid composition of the system includes a solution of about 10 parts by weight glycerol and about 87 parts by weight of a silver hydrosol (800 ppm colloidal silver). The second liquid composition of the system is an aqueous solution of 15 wt % peracetic acid. The two components are kept separate until immediately before the disinfectant is desired for use. The disinfectant solution is made by mixing the two components at about a 97:3 (first:second) weight ratio to yield a composition having about 0.4 wt % peracetic acid. It is noted that there will be less than 300 ppm by weight of the colloidal silver when based on the resultant disinfectant composition as a whole. This disinfectant solution can be used effectively to disinfect and sterilize a variety of surfaces.

Example 4

Preparation of a Concentrated Disinfectant Solution Using a Two-part System

A two-part disinfectant system is provided. The first liquid composition of the system is a solution of a silver alcosol (alcohol/ 3800 ppm silver). The second liquid composition of the system is an aqueous solution of 15 wt % peracetic acid. The two components are kept separate until immediately before the disinfectant is desired for use, and are admixed at a 17:13 (first:second) weight ratio. This resultant disinfectant solution can be further diluted using water. For example, 0.6 liters of the resultant disinfectant solution can be mixed with 2.4 liters of water to yield 3 liters of the disinfectant solution having 1.3 wt % PAA. This disinfectant solution can be used effectively to disinfect and sterilize a variety of surfaces.

Example 5

Preparation of a Disinfectant Solution Using a Two-part System

A two-part disinfectant system is provided. The first liquid composition includes, by weight, 9 parts ethanol, 40.9 parts water, and 0.1 part silver (2,000 ppm). The second liquid composition includes, by weight, 1.3 parts peroxypropanoic acid and 48.7 parts water. The two components are kept separate until immediately before the disinfectant is desired for use. The disinfectant solution is made by mixing the two components at about a 1:1 (first:second) weight ratio to yield a composition having about 1.3 wt % peroxypropanoic acid and about 1,000 ppm silver. In this embodiment, less than 3 wt % of hydrogen peroxide can be added to further stabilize the system. This disinfectant solution can be used effectively to disinfect and sterilize a variety of surfaces.

Example 6

Preparation of a Disinfectant Solution Using a Two-part System

A two-part disinfectant system is provided. The first liquid composition includes, by weight, 20 parts denatured alcohol, 29.45 parts water, and 0.05 parts silver and copper alloy (1,000 ppm). The second liquid composition is includes, by weight, 3 parts percitric acid and 47 parts water. The two components are kept separate until immediately before the disinfectant is desired for use. The disinfectant solution is made by mixing the two components at about a 1:1 (first: second) weight ratio to yield a composition having about 3 wt % percitric acid and about 500 ppm silver. In this embodiment, less than 3 wt % of hydrogen peroxide can be added to further stabilize the system. This disinfectant solution can be used effectively to disinfect and sterilize a variety of surfaces.

Example 7

Kill-time studies of *Mycobacterium bovis* Using a Resultant Disinfectant Solution A study was conducted to determine tuberculocidal activity when using resultant disinfectant solution which can be prepared in accordance with Example 1. The test was conducted on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfectants in the Absence and Presence of Bioburden. Journal of the American Dental Association, 119:493-505. 1989.

Specifically, a test suspension containing *Mycobacterium bovis* (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 µl of concentrated catalase solution (Sigma, C100, 42,300 units/mg).

The CRA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to Mycobacteria 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the 1:10$^3$ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 1a

*Mycobacterium bovis* Titer

| | Dilution | | |
|---|---|---|---|
| | $1:1 \times 10^3$ | $1:1 \times 10^4$ | $1:1 \times 10^5$ |
| Number of Colonies | TNC* TNC | TNC TNC | 175 174 |

*TNC—Too Numerous to Count

TABLE 1b

Disinfectant solution of Example 1
Dilution of *M. bovis*/disinfectant suspension

| | Dilution | | | |
|---|---|---|---|---|
| | Undiluted | $1:1 \times 10^1$ | $1:1 \times 10^2$ | $1:1 \times 10^3$ |
| 3 minutes | 1 | 0 0 | 0 0 | 0 0 |

TABLE 1c

Neutralization control
Undiluted 75
66

TABLE 1d

Sterility controls

| Material | Counts |
|---|---|
| Phosphate buffered gelatin | 0 |
| Neutralizer + catalas | 0 |
| Example 1 Disinfectant | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Inoculation of the test surface following drying produced a challenge exhibited by the water control. The initial concentration of viable bacilli on the test surface (So) was $2.63 \times 10^5$. Results from these procedures allowed log reduction (LR) and percent kill (PK) values to be calculated using the formulas: 1) LR=−Log (S/So) where S=concentration of viable organisms after a period of exposure to the disinfectant; and So=the initial concentration of viable organisms at time zero; These values are shown in the Table 20 below.

TABLE 2

Results

| Solution | Contact Time | Log Reduction (LR) | Percent Kill (PK) |
|---|---|---|---|
| Example 1 | 3 minutes | 5.02 | 99.99905 |

The neutralization control data indicated that each test solution was adequately neutralized. Observed counts were similar to those expected from the titer data.

Example 8

Kill-time Studies of Sporicidal Activity a Resultant Disinfectant Solution

A study was conducted to determine the antimicrobial activity of a silver-containing resultant disinfectant solution which can be prepared in accordance with Example 1. The study was conducted on bacterial endospores from the test organism *Bacillus subtilis*. This was accomplished by performing a standard kill-time suspension test using a suspension of *B. subtilis* endospores. In general, spores are much more difficult to kill than common bacteria.

The test suspension containing endospores from *Bacillus subtilis* (ATCC # 19659) was prepared from a culture grown for three days at 37° C. in Leighton-Doi medium. The suspension was placed at 65° C. for 30 minutes to kill vegetative organisms, then centrifuged to pellet the spores. Spores were resuspended in sterile HPLC water and allowed to set overnight at 4° C. This washing/setting process was repeated a total of three times. The final spore suspension was examined for purity using phase-contrast microscopy and stored at 4° C. until used.

A neutralizer solution was also prepared that consisted of 9 ml tubes of 12.7 wt % Tween 80, 6.0 wt % Tamol, 1.7 wt % lecithin, 1 wt % peptone, and 1.0 wt % cystine, and 500 mM tris (pH 7.85), to which 100 μl of catalase solution (Sigma, C100, 42,300 units/mg) was added immediately before use.

The "kill time" procedure was as follows: A 9.9 ml aliquot of the disinfectant was placed in a 50 ml polypropylene sterile centrifuge tube. The tube was equilibrated in a 20° C. water bath. The tube of disinfectant was inoculated with 100 μl of the spore suspension at time zero. After a 30 second contact time, one ml of spore/disinfectant suspension was removed to 9.1 ml of neutralizer. The tubes were mixed thoroughly. After 2 minutes, the neutralized suspension was serially diluted 1:10, in physiological saline solution in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension. A neutralizer control was performed by inoculating a mixture of 9.1 ml of neutralizer and 1 ml of disinfectant with 100 μl of the $1:1 \times 10^6$ dilution of the titer. This produced about 130 CFU/ml in the tube, which was allowed to stand for 20 minutes prior to dilution and assay by membrane filtration using duplicate 1 ml samples.

The results are provided as follows:

TABLE 3a

*Bacillus Subtilis* Titer

| | Dilution | | |
|---|---|---|---|
| | $1:1 \times 10^7$ | $1:1 \times 10^8$ | $1:1 \times 10^9$ |
| Number of | TNC* | 106 | 10 |
| Colonies | TNC | 115 | 15 |

*TNC—Too Numerous to Count

TABLE 3b

Disinfectant solution (Example 1)
Dilution of *B. subtilis* spores/disinfectant suspension

| | Dilution | | |
|---|---|---|---|
| | $1:1 \times 10^2$ | $1:1 \times 10^3$ | $1:1 \times 10^4$ |
| 30 Seconds | 0 | 0 | 0 |
| | 0 | 0 | 0 |

TABLE 3c

Neutralization control
Undiluted 135
118

TABLE 3d

Sterility Controls

| Material | Counts |
|---|---|
| PSS | 0 |
| Neutralizer | 0 |
| Columbia Agar | 0 |
| Example 1 | 0 |

Results of the titer showed a viable *B. subtilis* spore concentration of $1.11 \times 10^{10}$ spores per ml in the original suspension. Inoculation of 9.9 ml of disinfectant with 100 μl of this suspension produced an initial concentration of $1.11 \times 10^8$ spores per ml in the assay tube. Results from these procedures allowed log reduction (LR) and percent kill (PK) values to be calculated using the formulas: 1) LR=−Log (S/So) where S=concentration of viable organisms after specified contact time, and So=the initial concentration of viable organisms at time zero; and 2) PK=(1 −(S/So))×100. These values are shown below in Table 24.

TABLE 4

| | | Results | |
|---|---|---|---|
| Solution | Contact Time | Log Reduction (LR) | Percent Kill (PK) |
| Example 1 | 30 seconds | >7.05 | >99.999991 |

Neutralization control data revealed that the neutralizer was able to adequately neutralize this disinfectant. Observed counts were consistently higher than those expected. The test disinfectant solution of Example 1 had rapid and potent sporicidal activity. Specifically, the disinfectant solution of Example 1 was able to achieve greater than 7–log reduction within 30 seconds. As a control, the same culture was tested using the same concentration of peracetic acid with none of the other active ingredients (i.e. without the alcohol or silver content). The composition of Examples 1 exhibited a greater kill level by several orders of magnitude.

Example 9

Kill-time Studies of Sporicidal Activity Using 2.4% Alkaline Glutaraldehyde Disinfectant For comparison purposes, a study was conducted to determine the antimicrobial activity of a 2.4% alkaline glutaraldehyde disinfectant on bacterial endospores from the test organism *Bacillus subtilis* . Glutaraldehyde disinfectant solution is a common disinfectant used in hospitals to kill bacteria and other pathogens that might otherwise be difficult to kill. This study was carried out by performing a standard kill-time suspension test using a suspension of *B. subtilis* endospores. A 15 minute contact time was evaluated.

A test suspension containing endospores from *Bacillus subtilis* (ATCC # 19659) was prepared from a culture grown on Nutrient agar, to which additional sporulation enhancements were added. Plates were harvested with sterile water and endospores were purified by repeated centrifugations and resuspensions in water. The final wash was in 70 wt % ethanol for 30 minutes, to ensure the death of all vegetative bacteria. The spores were resuspended in water containing 0.1 wt % Tween 80 to prevent clumping and stored at 4° C. until used.

A neutralizer was prepared that consisted of 1 ml of freshly made, filter-sterilized sodium bisulfite solution at 5.28 wt %.

The "kill time" procedure was as follows: A 9.9 ml aliquot of the disinfectant was placed in a sterile glass culture tube. The tube was equilibrated in a 20° C. water bath. The tube of disinfectant, 9 ml of 2.4 wt % alkaline glutaraldehyde (Freshly activated CIDEXPLUS, 3.4 %, Lot #:2002247TP— diluted to 2.4 wt % with sterile water), was inoculated with 100 μl of the test organism suspension at time zero. After 15 min, 1 ml of spore/disinfectant suspension was removed to 9 ml of neutralizer. The tube was mixed thoroughly. After 2 minutes, the neutralized suspension was serially diluted (1:1× 10, 1:1×10$^2$, 1:1×10$^3$, etc.) in physiological saline solution (PSS). The number of viable spores in selected dilution tubes was assayed by membrane filtration. One (1) ml aliquots were plated in duplicate. The membranes were washed with about 100 ml of sterile PSS and removed to Columbia agar plates. The plates were incubated at 37° C. for 20 hours. The number of colonies on each filter was counted and log reduction and percent kill values were computed.

As a control, a titer of the test suspension was computed by performing membrane filtration assays on selected 1:10 dilutions in PSS of the test suspension.

A neutralizer control was performed by inoculating a mixture of 1 ml of neutralizer and 1 ml of disinfectant with 100 μl of the 1:1×10$^5$ dilution of the titer. This produced about 450 CFU/ml in the tube, which was allowed to stand for 20 minutes prior to dilution and assay by membrane filtration using duplicate 1 ml samples.

The results are provided as follows:

TABLE 5a

| | Titer | | |
|---|---|---|---|
| | | Dilution | |
| | 1:1 × 10$^6$ | 1:1 × 10$^7$ | 1:1 × 10$^8$ |
| Number of Colonies | TNC* TNC | 96 93 | 0 0 |

*TNC—Too Numerous to Count

TABLE 5b

Disinfectant solution (2.4 wt % alkaline glutaraldehyde disinfectant)
Dilution of *B. subtilis* spores/disinfectant suspension

| | Dilution | | | |
|---|---|---|---|---|
| | 1:1 × 10$^1$ | 1:1 × 10$^2$ | 1:1 × 10$^3$ | 1:1 × 10$^4$ |
| 15 minutes | TNC TNC | TNC TNC | TNC TNC | 259 52 |

TABLE 5C

| | Neutralization control | |
|---|---|---|
| | Dilution | |
| | 1:1 × 10$^1$ | 1:1 × 10$^2$ |
| 15 Seconds | 72 70 | 1 4 |

Sterilization controls indicated zero growth for the glutaraldehyde, sodium bisulfite, water, PSS, and Columbia agar. Results of the titer showed a viable *B. subtilis* spore concentration of 9.45×10$^8$ spores per ml in the original suspension. Inoculation of 9.9 ml of disinfectant with 100 μl of this suspension produced an initial concentration of 9.45×10$^6$ spores per ml in the assay tube. Results from these procedures allowed log reduction (LR) and percent kill (PK) values to be calculated using the formulas: 1) LR=−Log(S/So) where S=concentration of viable organisms after 1 hour, and So=the initial concentration of viable organisms at time zero; and 2) PK=(1−(S/So))×100. These values are shown below in Table 26.

TABLE 6

| | | Results | |
|---|---|---|---|
| Solution | Contact Time | Log Reduction (LR) | Percent Kill (PK) |
| Alkaline glutaraldehyde | 15 min | 0.48 | 67.1 |

Neutralization control data revealed that the neutralizer was able to adequately neutralize this disinfectant. Observed counts were greater than those expected. The 2.4 wt % alkaline glutaraldehyde solution tested had relatively slow sporicidal activity, producing only a 0.48 log-reduction in 15 minutes, which is significantly lower than that produced by any of the exemplary compositions above prepared in accordance with embodiments of the present invention.

Example 10

Kill-time Studies of *Mycobacterium bovis* Using Lysol® Spray

For comparison purposes, a study was conducted to determine tuberculocidal activity of a Lysol® spray disinfectant (Lysol Spray, spring waterfall scent Lot # B4194-NJ2 1413-A3) on a hard surface using the CRA Environmental Wipe Method. This method is fully described in: Christensen, R. P., R. A. Robison, D. F. Robinson, B. J. Ploeger, R. W. Leavitt, and H. L. bodily, Antimicrobial Activity of Environmental Surface Disinfectants in the Absence and Presence of Bioburden. Journal of the American Dental Association, 119:493-505. 1989.

Specifically, a test suspension containing *Mycobacterium bovis* (ATCC # 35743) was prepared from a frozen suspension of a standardized culture grown in modified Proskauer-Beck medium. The suspension was thawed and mixed with an equal volume of phosphate-buffered gelatin solution in a Teflon-on-glass tissue grinder on ice. The suspension was homogenized for two minutes, then diluted 1:4 in physiological saline solution (PSS) containing 0.1% Tween 80. The suspension was vortexed and held on ice until used in inoculate the test surface.

A neutralizer mixture consisted of 50 ml flasks of Tryptic soy broth containing 1.0% Tween 80, 1.0% lecithin, and 50 µl of concentrated catalase solution (Sigma, C100, 42,300 units/mg).

The CPA environmental Wipe Method which was used is detailed below. An 8×12 inch piece of laminated plastic counter covering was secured to polypropylene dental trays (size B, Zirc Dental) with silicone adhesive. Lids and trays were sterilized by a hydrogen peroxide gas plasma sterilizer. Two ml of test organism suspension was applied to the surface with a sterile 2×2-in cotton-filled gauze sponge. The surface was allowed to dry 20-30 minutes in a biosafety cabinet under laminar flow. Then 3.5 ml of disinfectant (or water) was applied to a sterile gauze sponge, which was used to wipe the inoculated test surface for 10 seconds using about 150-g pressure with overlapping strokes (20 left to right, followed by 20 top to bottom). After 3 minutes, the trays were flooded with 50 ml of neutralizer and scrubbed for 1 minute with a sterile polypropylene brush to remove and suspend organisms. The fluid was collected and serially diluted 1:10 in physiological saline solution (PSS). The number of viable organisms in selected dilution tubes was assayed by membrane filtration. One ml aliquots were plated in duplicate. The membranes were washed with about 100 ml of sterile PSS and removed to Mycobacteria 7H11 agar plates. The plates were incubated at 37° C. for about three weeks. The number of colonies on each was counted and log reduction and percent kill values were computed.

As a control, a titer of the test suspension was computed by performing membrane filtration assays of selected 1:10 dilutions of the test suspension in PSS. A neutralizer control was performed by inoculating a mixture of 9 ml of neutralizer and 1 ml of disinfectant with 100 µl of the 1:10³ dilution of the titer containing 1750 CFU. This produced 175 CFU/ml in the tube, which was allowed to stand for 20 minutes prior to dilution and assay of the tubes by membrane filtration using duplicate 1 ml samples.

The results are provided as follows:

TABLE 7a

| | Titer | | |
|---|---|---|---|
| | Dilution | | |
| | $1:1 \times 10^3$ | $1:1 \times 10^4$ | $1:1 \times 10^5$ |
| Number of Colonies | TNC* TNC | TNC TNC | 175 174 |

*TNC—Too Numerous to Count

TABLE 7b

Disinfectant solution (Lysol ® Spray)
Dilution of *M. bovis*/disinfectant suspension

| | Dilution | |
|---|---|---|
| | Undiluted | $1:1 \times 10^1$ |
| 3 minutes | TNC TNC | 640 486 |

TABLE 7c

Neutralization control
Undiluted 180
196

TABLE 7d

| Sterility controls | |
|---|---|
| Material | Counts |
| Phosphate buffered gelatin | 0 |
| Neutralizer + catalas | 0 |
| Lysol Spray | 0 |
| Mycobacteria 7H11 Agar | 0 |
| Physiological sterile saline (PSS) + 0.1% Tween 80 | 0 |
| Physiological sterile saline (PSS) | 0 |

Results of the titer showed the initial concentration of *M. bovis* was 1.75×107 CFU per ml in the prepared suspension. Inoculation of the test surface following drying produced a challenge exhibited by the water control. The initial concentration of viable bacilli on the test surface (So) was 2.63×10⁵. Results from these procedures allowed log reduction (LR) and percent kill (PK) values to be calculated using the formulas: 1) LR=–Log(S/So) where S=concentration of viable organisms after a period of exposure to the disinfectant; and So=the initial concentration of viable organisms at time zero; These values are shown in the Table 18 below.

TABLE 8

| | | Results | |
|---|---|---|---|
| Solution | Contact Time | Log Reduction (LR) | Percent Kill (PK) |
| Lysol ® Spray | 3 minutes | 0.97 | 89.3 |

The neutralization control data indicated that each test solution was adequately neutralized. Observed counts were similar to those expected from the titer data.

Example 11

Kill-rate Enhancement Using Alloys

To demonstrate the effectiveness of certain alloys in enhancing the kill rate of *B. Subtilis* bacteria, a composition comprising 0.5% by weight of hydrogen peroxide, 8% by weight ethanol, and the balance of water containing 300 ppm of a colloidal silver was prepared. A similar composition was prepared using identical components except that aqueous solution contained a silver alloy admixture with manganese (approximately 300 ppm silver and about 7 ppm manganese). A kill test was performed resulting in a 0.13 log reduction or a 25.6% kill rate of the *B. subtilis* after 30 seconds using the colloidal silver composition. The kill study was also performed using the colloidal silver-manganese alloy composition, which resulted in a 0.24 log reduction or 42.6% kill after 30 seconds.

Example 12

Residual Kill Properties of a Disinfectant Solution

The disinfectant solution of Example 1 is prepared as described. The solution is applied to a Petri dish containing bacterial colonies. The bacterial colonies are killed. The disinfectant solution is allowed to remain in the Petri dish until the disinfectant solution appears to be visibly gone, i.e. after solvent evaporation. New active bacterial colonies are transplanted onto the Petri dish without adding additional disinfectant solution. Within a period of 24 hours, the transplanted colonies are likewise killed.

Example 13

Residual Kill Properties of a Disinfectant Solution

The same as Example 12 except that the disinfectant solution is not made using a two-part system, but rather using direct admixing of the ingredients.

While the invention has been described with reference to certain preferred embodiments, those skilled in the art will appreciate that various modifications, changes, omissions, and substitutions can be made without departing from the spirit of the invention. It is therefore intended that the invention be limited only by the scope of the appended claims.

What is claimed is:

1. A two-part disinfectant system, comprising:
a first liquid composition and a second liquid composition, said first liquid composition comprising from 0.0005 ppm to 100,000 ppm by weight of a transition metal or alloy and an alcohol, and said second liquid composition comprising water and a peracid compound, and wherein said first and second liquid compositions are formulated to be combined so as to yield a resultant disinfectant solution.

2. A system as in claim 1, wherein the first liquid composition includes water.

3. A system as in claim 1, wherein the alcohol is present in the first liquid composition at from about 0.005 wt % to 99.99 wt %.

4. A system as in claim 1, wherein the alcohol is present in the first liquid composition at from 0.05 wt % to 80 wt %.

5. A system as in claim 1, wherein the alcohol is present in the first liquid composition at from 0.1 wt % to 50 wt %.

6. A system as in claim 1, wherein the alcohol is a $C_1$-$C_{24}$ alcohol.

7. A system as in claim 6, wherein $C_1$-$C_{24}$ alcohol is selected from the group consisting of methanol, ethanol, propanols, butanols, pentanols, and mixtures thereof.

8. A system as in claim 6, wherein the $C_1$-$C_{24}$ alcohol is a polyhydric alcohol.

9. A system as in claim 8, wherein the polyhydric alcohol is glycerol.

10. A system as in claim 8, wherein the polyhydric alcohol includes two alcohol groups.

11. A system as in claim 8, wherein the polyhydric alcohol includes three alcohol groups.

12. A system as in claim 1, wherein the transition metal or alloy thereof is a Group VI to Group XI transition metal or alloy thereof.

13. A system as in claim 1, wherein the transition metal or alloy thereof is a Group X to Group XI transition metal or alloy thereof.

14. A system as in claim 1, wherein the transition metal or alloy thereof is selected from the group consisting of ruthenium, rhodium, osmium, iridium, palladium, platinum, copper, gold, silver, manganese, zinc, alloys thereof, and mixtures thereof.

15. A system as in claim 1, wherein the transition metal or alloy thereof is a colloidal transition metal or alloy thereof.

16. A system as in claim 15, wherein the colloidal transition metal or alloy thereof is colloidal silver.

17. A system as in claim 15, wherein the colloidal transition metal or alloy thereof has an average particle size of from 0.001 µm to 1.0 µm.

18. A system as in claim 15, wherein the colloidal transition metal or alloy thereof has an average particle size of from 0.030 µm to 0.5 µm.

19. A system as in claim 1, wherein the transition metal or alloy thereof is an ionic transition metal.

20. A system as in claim 1, wherein the transition metal or alloy thereof is present in the first liquid composition at from 0.01 ppm to 20,000 ppm by weight.

21. A system as in claim 1, wherein the transition metal or alloy thereof is present in the first liquid composition at from 1 ppm to 5,000 ppm by weight.

22. A system as in claim 1, wherein the transition metal or alloy thereof is present in the resultant disinfectant solution at from 15 ppm to 1500 ppm by weight.

23. A system as in claim 1, wherein the peracid is an aliphatic peracid.

24. A system as in claim 1, wherein the peracid is an aromatic peracid.

25. A system as in claim 1, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

26. A system as in claim 1, wherein the peracid and any additional peroxygen is present in the second liquid composition at from 0.001 wt % to 80.0 wt %.

27. A system as in claim 1, wherein the peracid and any additional peroxygen is present in the second liquid composition at from 0.01 wt % to 30.0 wt %.

28. A system as in claim 1, wherein the peracid and any additional peroxygen is present in the second liquid composition at from 0.05 wt % to 15 wt %.

29. A system as in claim 1, wherein the peracid and any additional peroxygen is present in the resultant disinfectant solution at from 0.1 wt % to 10 wt %.

30. A system as in claim 1, wherein the peracid and any additional peroxygen is present in the resultant disinfectant solution at from 0.2 wt % to 5 wt %.

31. A system as in claim 1, wherein the peracid and any additional peroxygen is present in the resultant disinfectant solution at from 0.3 wt % to 2 wt %.

32. A system as in claim 1, further comprising a peroxide.

33. A system as in claim 32, wherein the peroxide is hydrogen peroxide.

34. A system as in claim 32, wherein the peroxide is a metal peroxide.

35. A system as in claim 34, wherein the metal peroxide is selected from the group consisting of sodium peroxide, magnesium peroxide, calcium peroxide, barium peroxide, and strontium peroxide, and mixtures thereof.

36. A system as in claim 32, wherein the peroxide is a peroxyhydrate.

37. A system as in claim 1, wherein the disinfectant solution is substantially free of aldehydes, chlorine and bromine-containing compositions, iodophore-containing compositions, phenolic-containing compositions, and quaternary ammonium-containing compositions.

38. A system as in claim 1, wherein the disinfectant solution can be diluted to a desired concentration using water.

39. A system as in claim 1, wherein the first liquid solution includes an alcosol.

40. A system as in claim 1, wherein the first liquid composition and the second liquid composition are in concentrated form, and wherein the compositions are formulated to accommodate additional water being added to at least one of the first liquid composition, the second liquid composition, and the resultant liquid solution in preparation for use.

41. A system as in claim 40, wherein the additional water is added to the first liquid composition in preparation for use.

42. A system as in claim 40, wherein the additional water is added to the second liquid composition in preparation for use.

43. A system as in claim 40, wherein the additional water is added to the resultant disinfectant solution in preparation for use.

44. A method of disinfecting a surface, comprising:
admixing a first liquid composition and a second liquid composition to form a resultant disinfectant solution, said first liquid composition comprising from 0.0005 ppm to 100,000 ppm by weight of a transition metal or alloy and an alcohol, said second liquid composition comprising water and a peracid compound; and
contacting the resultant disinfectant solution with a surface, thereby disinfecting the surface.

45. A method as in claim 44, wherein the admixing step further includes adding additional water to at least one of the first liquid composition, the second liquid composition, and the resultant liquid solution in preparation for use.

46. A method as in claim 45, wherein the additional water is added to the first liquid composition in preparation for use.

47. A method as in claim 45, wherein the additional water is added to the second liquid composition in preparation for use.

48. A method as in claim 45, wherein the additional water is added to the resultant disinfectant solution in preparation for use.

49. A method as in claim 44, wherein the first liquid composition includes water.

50. A method as in claim 44, wherein the alcohol is present in the first liquid composition at from about 0.005 wt % to 99.99 wt %.

51. A method as in claim 44, wherein the alcohol is present in the first liquid composition at from 0.1 wt % to 50 wt %.

52. A method as in claim 44, wherein the alcohol is a $C_1$-$C_{24}$ alcohol.

53. A method as in claim 52, wherein the $C_1$-$C_{24}$ alcohol is a polyhydric alcohol.

54. A method as in claim 53, wherein the polyhydric alcohol is glycerol.

55. A method as in claim 44, wherein the transition metal or alloy thereof is selected from the group consisting of ruthenium, rhodium, osmium, iridium, palladium, platinum, copper, gold, silver, manganese, zinc, alloys thereof, and mixtures thereof.

56. A method as in claim 44, wherein the transition metal or alloy thereof is a colloidal transition metal or alloy thereof.

57. A method as in claim 56, wherein the colloidal transition metal or alloy thereof is colloidal silver.

58. A method as in claim 57, wherein the colloidal transition metal or alloy thereof has an average particle size of from 0.030 μm to 0.5 μm.

59. A method as in claim 44, wherein the transition metal or alloy thereof is an ionic transition metal.

60. A method as in claim 44, wherein the transition metal or alloy thereof is present in the first liquid composition at from 0.01 ppm to 20,000 ppm by weight.

61. A method as in claim 44, wherein the transition metal or alloy thereof is present in the resultant disinfectant solution at from 15 ppm to 1,500 ppm by weight.

62. A method as in claim 44, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

63. A method as in claim 44, wherein the peracid is present in the second liquid composition at from 0.01 wt % to 30.0 wt %.

64. A method as in claim 44, wherein the peracid is present in the resultant disinfectant solution at from 0.1 wt % to 10 wt %.

65. A method as in claim 44, wherein the peracid is present in the resultant disinfectant solution at from 0.2 wt % to 5 wt %.

66. A method as in claim 44, wherein the peracid further comprises a peroxide.

67. A method as in claim 44, wherein the disinfectant solution is substantially free of aldehydes, chlorine and bromine-containing compositions, iodophore-containing compositions, phenolic-containing compositions, and quaternary ammonium-containing compositions.

68. A method as in claim 44, wherein the first liquid solution includes an alcosol.

69. A method as in claim 44, wherein the contacting step occurs after the resultant disinfectant solution is formed.

70. A method as in claim 44, wherein the contacting step occurs by contacting the first liquid solution and the second liquid solution with the surface such that the resultant disinfectant solution is formed while in contact with the surface.

71. A method of disinfecting and providing residual kill at a surface comprising:
contacting said surface with a disinfectant solution according to present claim 1, wherein, after drying, residual components of the disinfectant solution are allowed to remain on the surface causing residual kill of bacterial, viral, or fungal organisms that subsequently contact the surface.

72. A method as in claim 71, wherein the alcohol is present in the disinfectant solution at from about 0.005 wt % to 99.99 wt %.

73. A method as in claim 71, wherein the alcohol is present in the disinfectant solution at from 0.1 wt % to 50 wt %.

74. A method as in claim 71, wherein the alcohol is a $C_1$-$C_{24}$ alcohol.

75. A method as in claim 71, wherein the alcohol is a polyhydric alcohol.

76. A method as in claim 71, wherein the transition metal or alloy thereof is selected from the group consisting of ruthenium, rhodium, osmium, iridium, palladium, platinum, copper, gold, silver, manganese, zinc, alloys thereof, and mixtures thereof.

77. A method as in claim 71, wherein the transition metal or alloy thereof is a colloidal transition metal or alloy thereof.

78. A method as in claim 77, wherein the colloidal transition metal or alloy thereof has an average particle size of from 0.030 μm to 0.5 μm.

79. A method as in claim 71, wherein the transition metal or alloy thereof is an ionic transition metal.

80. A method as in claim 71, wherein the transition metal or alloy thereof is present in the disinfectant solution at from 15 ppm to 1,500 ppm by weight.

81. A method as in claim 71, wherein the peracid is selected from the group consisting of peroxyformic acid, peroxyacetic acid, peroxyoxalic acid, peroxypropanoic acid, perlactic acid, peroxybutanoic acid, peroxypentanoic acid, peroxyhexanoic acid, peroxyadipic acid, peroxycitric, peroxybenzoic acid, and mixtures thereof.

82. A method as in claim 71, wherein the peracid further comprises present in the disinfectant solution at from 0.1 wt % to 10 wt %.

83. A method as in claim 71, wherein the peroxygen is a peroxide.

84. A method as in claim 71, wherein the disinfectant solution is substantially free of aldehydes, chlorine and bromine-containing compositions, iodophore-containing compositions, phenolic-containing compositions, and quaternary ammonium-containing compositions.

85. A method as in claim 71, wherein the disinfectant solution is prepared by direct admixing of individual ingredients.

* * * * *